United States Patent [19]

Buchs et al.

[11] Patent Number: 5,814,635

[45] Date of Patent: Sep. 29, 1998

[54] CONCENTRATED INJECTION SOLUTION OF ALKALI METAL SALTS OF REDUCED FOLATES

[75] Inventors: Peter Buchs, Agra; Fabrizio Marazza, Novaggio, both of Switzerland

[73] Assignee: Cerbios-Pharma S.A., Switzerland

[21] Appl. No.: 886,942

[22] Filed: Jul. 2, 1997

Related U.S. Application Data

[63] Continuation of Ser. No. 388,431, Feb. 14, 1995, abandoned.

[30] Foreign Application Priority Data

Feb. 14, 1994 [CH] Switzerland .......................... 00432/94

[51] Int. Cl.$^6$ ...................... A61K 31/505; C07D 475/04
[52] U.S. Cl. .......................... 514/249; 514/823; 544/258
[58] Field of Search ............................. 424/400; 514/249, 514/258, 823; 544/258, 259, 260

[56] References Cited

U.S. PATENT DOCUMENTS

| | | | |
|---|---|---|---|
| 2,695,860 | 11/1954 | Weidenheimer et al. | |
| 2,741,608 | 4/1956 | Shive | 544/258 |
| 4,350,659 | 9/1982 | Riceberg | 422/61 |
| 4,931,441 | 6/1990 | Lawrence | 514/249 |
| 5,124,452 | 6/1992 | Gennari | |
| 5,173,488 | 12/1992 | Haeger | 514/249 |
| 5,177,076 | 1/1993 | Nijkerk et al. | 514/249 |

FOREIGN PATENT DOCUMENTS

| | | |
|---|---|---|
| 0293029 | 11/1988 | European Pat. Off. . |
| 0401895 | 12/1990 | European Pat. Off. . |
| 0416232 | 3/1991 | European Pat. Off. . |
| WO90/10460 | 9/1990 | WIPO . |
| 95/26963 | 10/1995 | WIPO . |

*Primary Examiner*—Robert H. Harrison
*Attorney, Agent, or Firm*—Burns, Doane, Swecker & Mathis, L.L.P.

[57] ABSTRACT

A concentrated, stable solution, especially an injection solution, which comprises water and either sodium-leucovorin or potassium-leucovorin or sodium-N(5)-methyl-5,6,7,8-tetrahydrofolic acid or potassium-N(5)-methyl-5,6,7,8-tetrahydrofolic acid. Also described is a process for the preparation of the solution, as well as its uses.

22 Claims, No Drawings

CONCENTRATED INJECTION SOLUTION OF ALKALI METAL SALTS OF REDUCED FOLATES

This application is a continuation of application Ser. No. 08/388,431, filed Feb. 14, 1995, now abandoned.

The present invention is directed to a concentrated, stable solution, especially an injection solution, and to a process for the preparation of this injection solution.

N(5)-Formyl-5,6,7,8-tetrahydrofolic acid, also named folinic acid, is used in the form of its calcium salt (calcium-leucovorin USP) as an agent in the cancer chemotherapy.

This agent is used not only for rescues (rescue agent) after the treatment with high doses of the cytostatic agent methotrexate bus also in combination with the anticancer agent 5-fluorouracil (5-FU).

See for example:
1. The clinical pharmacology of methotrexate, J. H. Schornagel and J. G. McVie, Cancer Treatment Reviews (1983), 10, 53.
2. The biochemical modulation of 5-FU through Leucovorin, M. Borner, K. Brunner. Schweiz. Med. Wschr., (1991), 121, 1149.

Folinic acid is also used for the treatment of megaloblastic anaemiae and a dihydropteridin reductase deficiency.

These therapeutic uses of folinic acid require sometimes the intravenous administration of high doses, for example 100 to 200 mg/m$^2$ of body surface.

Because calcium-leucororin is relatively poorly soluble in water (about 1% by weight at room temperature) there exists an intense need of a formulation which contains a higher concentration of the active principle.

With such high concentrations it is possible to avoid that unacceptable high doses of solution must be injected.

When, according to a personal communication of Dr. C. Young from the Memorial Sloan Kettering Cancer Center in New York, 5-FU and leucovorin are combined within the same infusate as a part of a continuous infusion regimen of 5-FU, then the presence of calcium ions contribute to catheter blockage.

Unless the leucovorin content is reduced greatly, catheter blockage by a precipitate becomes a recurrent problem.

The precipitate is reported to be calcium carbonate, presumably formed by the reaction of calcium with plasma bicarbonate at or in the near of the catheter tip.

The therapeutic utility of leucovorin could be enhanced by the availability of a more soluble calcium free leucovorin-salt.

In the prior art are known up to now two injection solutions on the basis of folates:

A. In the European patent application Nr. 90 112 426.3, publication Nr. 0 416 232 A2 is described a stable injectable pharmaceutical formulation for folic acid and leucovorin.

This formulation contains beside a water-soluble, pharmaceutically acceptable salt of folic acid or leucovorin various stabilizers, such as benzyl alcohol, tromethamine and monothioglycerol.

This formulation may contain in maximum 2.5% of calcium-leucovorin.

The various stabilizers are undoubtedly a drawback, because individual components are not described in all pharmacopeias as pharmacologically acceptable in injectable preparations.

B. In the European patent application Nr. 90 201 353.1, publication Nr. 0 401 895 A1 is described an aqueous calcium-folinate solution, which is stable at refrigerator temperature. This solution must contain a complexing agent for calcium.

As the only complexing agent is mentioned ethylene diamine-tetraacetate (EDTA).

This solution may contain in maximum 2.7% of calcium-folinate.

EDTA and similar complexing agents are not acceptable as components in an injection solution.

It is an object of the present invention to overcome the above mentioned drawbacks.

It is a further object of the present invention to provide a concentrated, stable solution on the basis of folates, which contains neither a stabilizer nor a completing agent.

It has been found now quite surprisingly, that the inventive solutions are stable for at least 12 months at temperatures from 0° C. to 5° C. without the addition of stabilizers and/or complexing agents.

The inventive concentrated stable solution, especially an injection solution, is characterized in that it contains besides water either sodium-leucovorin or potassium-leucovorin or sodium-N(5)-methyl-5,6,7,8-tetrahydrofolic acid or potassium-N(5)-methyl-5,6,7,8-tetrahydrofolic acid.

The inventive process for the preparation of an inventive concentrated, stable solution, especially an injection solution, is characterized in that folinic acid or N(5)-methyl-5,6,7,8-tetrahydrofolic acid is suspended in water, which is degassed and which is acceptable for the preparation of injection solutions, at room temperature under an inert gas atmosphere, then is added an aqueous solution of sodium- or potassium-hydroxide, -hydrogen carbonate or -carbonate in portions during such a long time until a clear solution is formed, which has the at times desired pH-value, subjecting the obtained solution to a sterile filtration, and filling the obtained sterile solution under an inert gas atmosphere in vials.

Among the preferred embodiments of the present invention, the concentrated solution is characterized in that it contains from 2 to 15% by weight, preferably from 2 to 6% by weight, and more preferably 5% by weight, of sodium-leucovorin or potassium-leucovorin or sodium-N(5)-methyl-5,6,7,8-tetrahydrofolic acid or potassium-N(5)-methyl-5,6,7,8-tetrahydrofolic acid.

The pH-value of the solution can range from 7.5 to 8.5, preferably 7.9 to 8.1, and more preferably 8.0.

The solution can be filled in vials having in their interior an inert gas atmosphere, especially a nitrogen atmosphere.

Also provided is a process for the preparation of the concentrated, stable solution, which can be used as an injection solution. Folinic acid or N(5)-methyl-5,6,7,8-tetrahydrofolic acid is suspended in degassed water at room temperature under an inert gas atmosphere. The water is acceptable for the preparation of injection solutions. An aqueous solution of sodium- or potassium-hydroxide, -hydrogen carbonate or -carbonate is added in portions for a sufficient time until a clear solution is formed, which has the desired pH-value. The obtained solution is subjected to sterile filtration, and vials are filled with the resulting sterile solution under an inert gas atmosphere.

The solution can be used in the preparation of a medicament for rescues/rescue agents after treatments with high doses of methotrexate. The inventive solution also has applicability in the preparation of a medicament, combined with 5-fluorouracil. The solution can additionally be used in the preparation of a medicament for the treatment of megaloblastic anaemiae and dihydropteridin reductase deficiency.

The following example illustrates the present invention.

EXAMPLE 200.7 g of folinic acid with a water content of 10.2% by weight—for example prepared according to E. Khalifa, A.

N. Ganguly, J. H. Bieri and M. Viscontini, Helv. Chim. Acta, Vol 63, 2554, (1980)—were suspended under stirring at room temperature in 2.5 liters of degassed, sterile water under a nitrogen atmosphere.

Then was added drop by drop under stirring a 10% aqueous sodium hydroxide solution until a clear solution has been formed, which had a pH-value of 8.0.

The obtained clear solution was diluted to a volume of 3.6 liters by the addition of degassed, sterile water.

This diluted solution was subjected to a sterile filtration (pore size: 0.2 micrometer).

The obtained sterile filtrate was filled under a nitrogen atmosphere in vials.

The vials were stored in a refrigerator at a temperature of 4° C.

Thereby were obtained the following stability datas for the solution filled in vials:

| time (months) | content in % (HPLC-analysis) |
| --- | --- |
| 0 | 100 |
| 3 | 99.0 |
| 6 | 96.8 |
| 12 | 95.2 |

After 12 months the solution was still clear; no precipitates were observed.

We claim:

1. A concentrated, stable solution, comprising water and sodium-leucovorin, potassium-leucovorin, sodium-N(5)-methyl-5,6,7,8-tetrahydrofolic acid or potassium-N(5)-methyl-5,6,7,8-tetrahydrofolic acid, in the absence of tromethamine, monothioglycerol and benzyl alcohol, exhibiting no precipitate at 0°–5° C. for at least 6 months.

2. A solution according to claim 1, wherein the solution is an injection solution.

3. A solution according to claim 1, wherein the content of the sodium-leucovorin, potassium-leucovorin, sodium-N(5)-methyl-5,6,7,8-tetrahydrofolic acid, or potassium-N(5)-methyl-5,6,7,8-tetrahydrofolic acid in the solution is in the range of from about 2 to 15% by weight.

4. A solution according to claim 3, wherein the content of the sodium-leucovorin, potassium-leucovorin, sodium-N(5)-methyl-5,6,7,8-tetrahydrofolic acid, or potassium-N(5)-methyl-5,6,7,8-tetrahydrofolic acid in the solution is in the range of from about 2 to 6% by weight.

5. A solution according to claim 4, wherein the content of the sodium-leucovorin, potassium-leucovorin, sodium-N(5)-methyl-5,6,7,8-tetrahydrofolic acid, or potassium-N(5)-methyl-5,6,7,8-tetrahydrofolic acid in the solution is about 5% by weight.

6. A solution according to claim 1, wherein the solution has a pH-value in the range of from about 7.5 to 8.5.

7. A solution according to claim 6, wherein the pH-value of the solution is in the range of from about 7.9 to 8.1.

8. A solution according to claim 7, wherein the pH-value of the solution is about 8.0.

9. A solution according to claim 1, wherein the solution is filled in vials having in their interior an inert gas atmosphere.

10. A solution according to claim 9, wherein the inert gas atmosphere is a nitrogen atmosphere.

11. A process for the preparation of the concentrated, stable solution according to claim 1, comprising suspending folinic acid or N(5)-methyl-5,6,7,8-tetrahydrofolic acid in degassed water, at room temperature under an inert gas atmosphere, the water being acceptable for preparing an injection solution, adding an aqueous solution of sodium- or potassium-hydroxide, sodium- or potassium-hydrogen carbonate or sodium- or potassium-carbonate in portions to the suspension until a clear solution is formed, subjecting the obtained clear solution to a sterile filtration, and filling the obtained sterile solution under an inert gas atmosphere in vials.

12. A process according to claim 11, wherein the stable solution is an injection solution.

13. A process according to claim 11, wherein the content of the sodium-leucovorin, potassium-leucovorin, sodium-N(5)-methyl-5,6,7,8-tetrahydrofolic acid, or potassium-N(5)-methyl-5,6,7,8-tetrahydrofolic acid in the clear solution is in the range of from about 2 to 15% by weight.

14. A process according to claim 13, wherein the content of the sodium-leucovorin, potassium-leucovorin, sodium-N(5)-methyl-5,6,7,8-tetrahydrofolic acid, potassium-N(5)-methyl-5,6,7,8-tetrahydrofolic acid in the clear solution is in the range of from about 2 to 6% by weight.

15. A process according to claim 11, wherein the clear solution has a pH-value in the range from about 7.5 to 8.5.

16. The process according to claim 15, wherein the pH-value of the clear solution is in the range of from about 7.9 to 8.1.

17. A medicament for rescues/rescue agents formed from a solution according to claim 1.

18. A medicament for rescues/rescue agents after treatments with high doses of methotrexate, formed from a solution according to claim 1.

19. A medicament comprising the combination of a solution according to claim 1 and 5-fluorouracil.

20. A medicament for treating megaloblastic anaemiae and dihydropteridin reductase deficiency formed from a solution according to claim 1.

21. A process according to claim 14, wherein the content of the sodium-leucovorin, potassium-leucovorin, sodium-N(5)-methyl-5,6,7,8-tetrahydrofolic acid, or potassium-N(5)-methyl-5,6,7,8-tetrahydrofolic acid in the clear solution is about 5% by weight.

22. The process according to claim 16, wherein the pH-value of the clear solution is about 8.0.

* * * * *